United States Patent [19]

Wilkins

[11] Patent Number: 5,272,926
[45] Date of Patent: Dec. 28, 1993

[54] MICROBIAL RETRIEVAL AND SAMPLING PIPETTE WITH A REMOVABLE COVER

[76] Inventor: Judd R. Wilkins, 281 Littletown Quarter, Williamsburg, Va. 23185

[21] Appl. No.: 791,467
[22] Filed: Nov. 13, 1991
[51] Int. Cl.$^5$ .............................................. G01N 1/14
[52] U.S. Cl. ............................... 73/864.13; 73/864.16; 422/100
[58] Field of Search ............ 73/864.01, 864.13, 864.14, 73/864.16, 864.17, 864.18; 422/100

[56] References Cited

U.S. PATENT DOCUMENTS

| | | | |
|---|---|---|---|
| 3,603,156 | 9/1971 | Konkol | 422/100 |
| 3,732,734 | 5/1973 | Avakian | 73/864.14 |
| 3,991,617 | 11/1976 | d'Autry | 73/864.14 |
| 4,009,611 | 3/1977 | Koffer | 73/864.14 |
| 4,151,750 | 5/1979 | Suovaniemi | 73/864.14 |
| 4,248,830 | 2/1981 | Kallies et al. | 422/100 |
| 4,283,950 | 8/1981 | Tervamaki | 73/864.14 |
| 4,487,081 | 12/1984 | De Vaughn et al. | 73/864.16 |

FOREIGN PATENT DOCUMENTS

| | | | |
|---|---|---|---|
| 3701250 | 7/1988 | Fed. Rep. of Germany | 422/100 |
| 2215404 | 9/1989 | United Kingdom | 422/100 |

*Primary Examiner*—Hezron E. Williams
*Assistant Examiner*—Nashmiya Ashraf
*Attorney, Agent, or Firm*—Wallace J. Nelson

[57] ABSTRACT

This invention (FIGS. 1-4) relates to a pipette-syringe combination employing a wire probe attached to the syringe plunger to remove a cover provided over the pipette orifice. One edge of the protective cover is attached via an elastomeric strap to the pipette. When the cover is forced away from the pipette orifice, the elastomeric strap pulls the cover away from, and prevents return of the cover over, the pipette orifice. A suitable sample may then be drawn in the pipette at the location of the cover removal. In the embodiment of FIGS. 5-7, the protective cover is manually removed to obtain a surface growth sample by the wire probe and the sample retracted within the pipette. A quantity of nutrient broth is added to the pipette, the pipette sealed by manually replacing the protective cover, with subsequent incubation of the sealed pipette in an incubator. After incubation, the pipette is agitated to distribute the growth, the cover is manually removed and controlled quantities of the broth transferred to a number of tubes for further study.

6 Claims, 2 Drawing Sheets

MICROBIAL RETRIEVAL AND SAMPLING PIPETTE WITH A REMOVABLE COVER

FIELD OF THE INVENTION

This invention relates generally to sampling devices and relates specifically to a pipette-syringe combination retrieval and sampling device having a remotely removable, protective cover disposed over the orifice thereof.

BACKGROUND OF THE INVENTION

In the field of science, especially in microbiology, the need to obtain a representative sample is a constant challenge. It has been often quoted "that a laboratory test is only as good as the sample." This requirement for a representative sample applies, not only to those specimens from a clinical source, industrial processes, or polluted water, but also includes daily operations in the laboratory. For example, a classical microbiological technique is the retrieval and transfer of growth from a tube of nutrient broth. In the usual procedure a loop of growth is removed and streaked on an agar surface or transferred to another tube of broth for further incubation. In some cases a sterile pipette is used instead of a wire loop.

In order to encourage the growth of a wide range of organisms, a small amount of agar (0.1%) may be added to nutrient broth. This amount of agar supports the development of obligate anaerobes, micro-aerophiles and aerobes growing in layers with aerobes at the surface and anaerobes at the bottom of the growth container. If the concentration of agar is increased to a range of 0.16 to 0.4%, subsurface colonies will develop ranging in shape from elongated, diffuse to compact tear shaped. This concentration is generally referred to as soft agar. Microbial growth under these conditions does not readily lend itself to transfer with either a wire loop or pipette, since as the loop or pipette is moved through the layers of growth, contamination occurs before the desired area of growth is reached. There is therefore a definite need in the art for an apparatus for retrieving a representative uncontaminated sample of bacterial growth from specific areas within a growth medium. Subsurface bacterial colony growth in soft agar is further elaborated on in applicant's co-pending patent application, Ser. No. 07/751,182 filed Aug. 28, 1991, and the subject matter of which is incorporated by reference herein.

It is an object of the present invention to provide an improved pipette-syringe combination that permits retrieval of organism samples in a specific area of growth without prior contamination of the sampling device by surrounding media.

Another object of the present invention is an improved pipette-syringe combination that is operable in agar containing and agar free media.

A further object of the present invention is an apparatus and process for retrieving a representative sample from subsurface growth in a media source.

An additional object of the present invention is an apparatus capable of recovering organisms at various depths in water columns of eco-systems.

Still another object of the present invention is a novel liquid sampling device for the collection of liquid samples from various depths of samples or containers of polluted water, fermentation liquids, food processing operations, and the like.

Another object of the present invention is a novel sampling pipette that also can serve as a growth chamber for the collected sample.

Yet another object of the present invention is a process of obtaining a representative sample in a pipette, adding nutrient broth to the pipette and incubating the sample in the nutrient broth containing pipette before transferring the accumulated culture growth to a number of tubes.

SUMMARY OF THE INVENTION

The foregoing and additional objects are attained, according to one aspect of the present invention, by providing a wire probe inside a conventional plastic pipette-syringe combination and securing the wire probe to the bottom of the pipette plunger in the syringe. The length of the wire probe is selected such that the unattached end thereof is maintained within the pipette when the plunger is retracted and is extended a controlled distance from the pipette sampling orifice when the plunger is fully depressed.

By providing the wire probe attached to the plunger, the movement of the wire probe inside the pipette is controlled by the pulling and pushing action of the plunger inside the barrel of the syringe. A removable plastic cap is disposed over the pipette orifice and has one edge surface thereof attached to the exterior of the pipette wall via an elastic strap. The downward motion of the wire probe, responsive to pushing on the plunger, pushes the removable cap away from the pipette orifice and the elastic strap acting on the edge of the cap retracts the cap away from, and prevents the cap from again covering, the pipette orifice as the wire probe is retracted by an upward pull of the syringe barrel. The upward pull of the plunger simultaneously creates a suction force that forces sample to flow into the pipette. The plastic pipette-syringe combination is designed as a sterile disposable, or "one use only" unit.

In another aspect of the present invention, the removable cap is removed by the same wire probe, or by hand, and the wire probe extended to touch the surface colony from the surface of a petri dish. The wire probe is then retracted, the tip of the pipette placed in nutrient broth and sterile media drawn into the pipette by the pulling action of the plunger-syringe barrel. The orifice cover is then manually placed over the pipette tip for hermetically sealing of the pipette orifice. The entire pipette is then placed in an incubator for 18 to 24 hours at the desired temperature, usually 37° C. The accumulated growth is then uniformly distributed by a back-and-forth rocking motion of the pipette and, after manual removal of the orifice cover, the growth can be accurately transferred to a number of tubes by a downward action of the syringe plunger.

In each aspect of the present invention, the plastic pipette-syringe combination is designed to be a disposable, "one use only" unit.

BRIEF DESCRIPTION OF THE DRAWINGS

A more complete appreciation of the invention and many of the attendant advantages thereof will be more readily apparent as the same becomes better understood by reference to the following detailed description when considered in connection with the accompanying drawings wherein.

DETAILED DESCRIPTION

Figure 1:
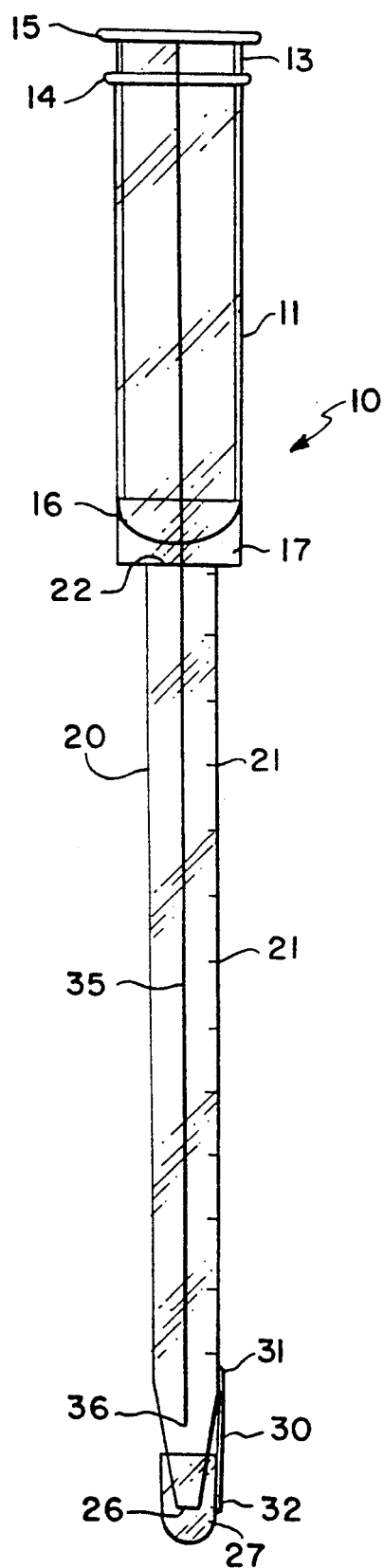
FIG. 1 is a part schematic view of a disposable pipette-syringe combination according to one aspect of the present invention.
Figure 2:
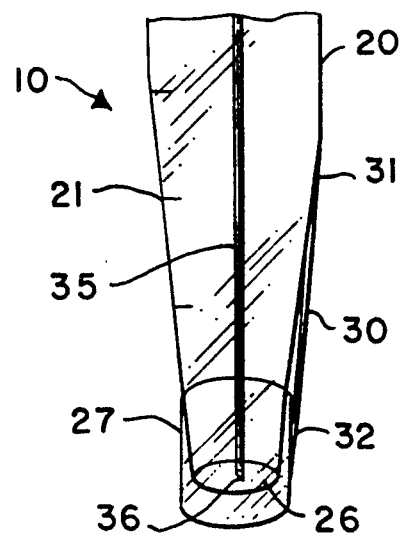
FIG. 2 is an enlarged view of the tip end of the pipette-syringe combination shown in FIG. 1.

Referring now to the drawings and more particularly to FIGS. 1 and 2, there is shown a part schematic view of the preferred embodiment of a disposable pipette-syringe combination, according to the present invention and designated generally by reference numeral 10. A first end of pipette 10 is formed of an elongated syringe barrel 11 having a plunger 13 slidably disposed therein. One end of barrel 11 is provided with an external bead 14 and serving to limit the movement of plunger 13 therein.

Plunger 13 is provided with a beaded end 15 that engages bead 14 on barrel 11 when the plunger is fully depressed. The other end of plunger 13 is provided with a rounded end 16 that engages the bottom 17 of barrel 11 when the plunger is fully depressed. An elongated, hollow, pipette tube 20, having graduated indicia 21 thereon, has one end secured in fluid communication with an opening 22 in the bottom 17 of barrel 11.

Pipette tube 20 is provided with a tapered tip terminating in an orifice 26. A removable, plastic, protective cover 27 is disposed over orifice 26 and extends over a portion of the length of tube 20. An elastomeric strap 30 is attached at one end to the exterior of pipette tube 20, as designated by reference numeral 31. The other end of elastomeric strap 30 is secured to an edge surface of removable cover 27, as designated by reference numeral 32. Elastomeric strap 30 is under tension when orifice cover 27 is disposed over pipette orifice 26, as illustrated in FIGS. 1 and 2.

An elongated wire probe 35 is secured to the rounded end 16 of plunger 13 and extends through opening 22 and along the internal hollow portion of pipette tube 20. The length of wire probe 35 is selected such that the unattached blunt end 36 thereof is maintained within the pipette tube 20 when plunger 13 is retracted, and is extended a controlled distance from pipette tube orifice 26, when plunger 13 is fully depressed, or when rounded end 16 thereof is in engagement with bottom 17 of barrel 11.

Figure 3:
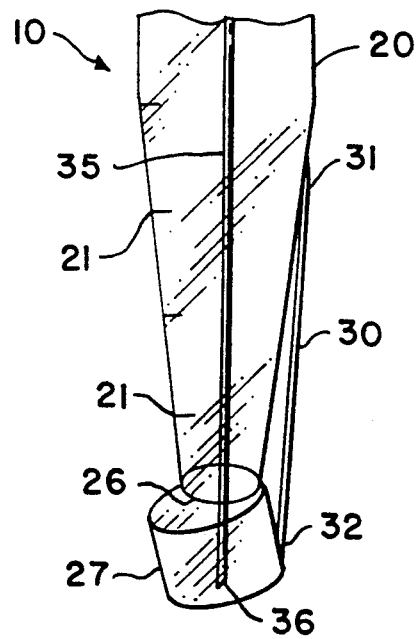
FIG. 3 is a view similar to FIG. 2 and illustrating the forced removal of the pipette orifice cover by the wire probe.

Referring now more particularly to FIG. 3, wire probe 35 is shown depressed (via movement of plunger 13) sufficiently for blunt end 36 thereof to engage the bottom of, and start movement of cover 27 away from its orifice covering position. Protective cover 27 is frictionally disposed on pipette tube 20 but is removable therefrom by the force of wire probe 35 acting against the interior bottom surface thereof. The construction of the bottom surface of cover 27 is of adequate thickness, or provided with suitable covering, to prevent puncture thereof by the blunt end 36 of wire probe 35 during removal.

Figure 4:
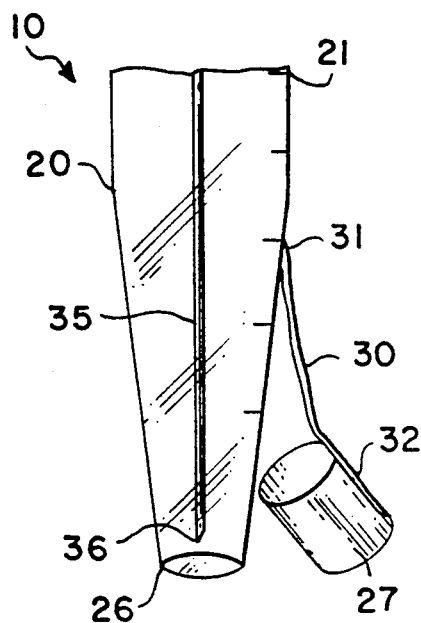
FIG. 4 is a view similar to FIGS. 1 and 2 and illustrating the elastomeric retraction of the orifice cover from the pipette orifice.

As illustrated, the tension of elastomeric strap 30 acting on cover 27 causes protective cover 27 to tilt at an angle once an edge thereof clears the end of pipette tube 20 and orifice 26. As probe wire 35 is retracted back into pipette 20, tension on elastomeric strap 30 is no longer maintained and the elastomeric strap 30 pulls orifice protective cover 27 to the side of pipette 10 and prevents it from returning to cover orifice 25 (FIG. 4). The removal of protective cover 27 from orifice 26 is accomplished entirely by the action of plunger 13, probe wire 35 and elastomeric strap 30. Thus, pipette tube 20 may be inserted through soft agar or fluid media to the exact point from which it is desired to obtain a sample without exposing orifice 26 to possible contaminants away from the media surrounding the sample area.

Figure 5:
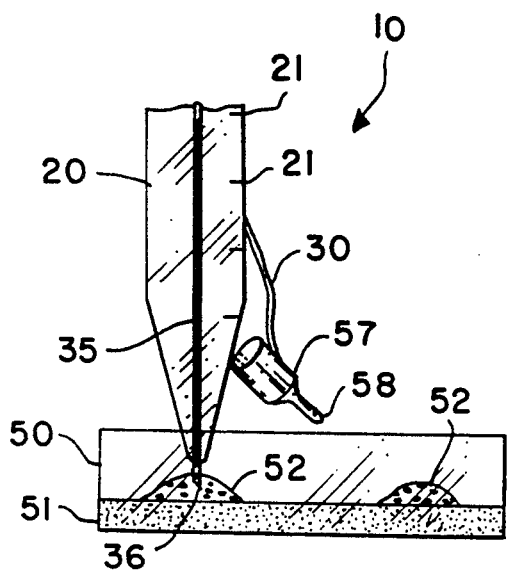
FIG. 5 is a part sectional, part schematic view showing a slight modification of the pipette orifice cover and illustrating direct sampling by the wire probe from a colony growth in a petri dish.
Figure 6:
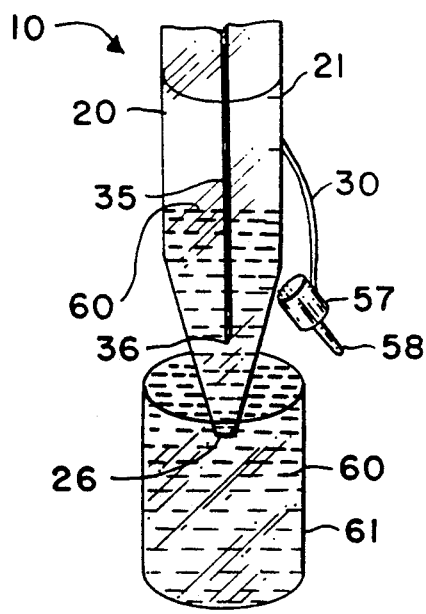
FIG. 6 is a part schematic illustration of the pipette structure shown in FIG. 5 in position to extract a quantity of growth medium from a container of nutrient broth.
Figure 7:
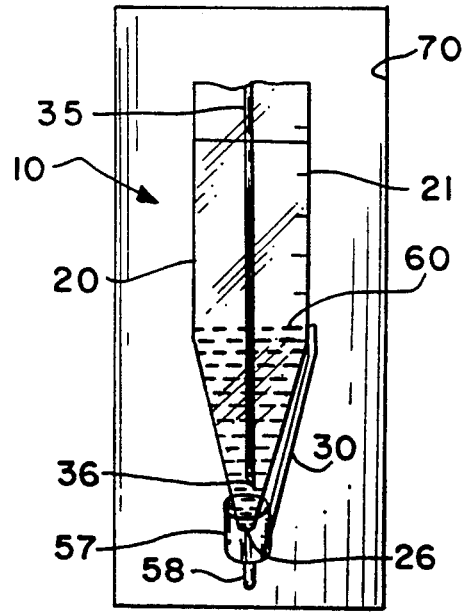
FIG. 7 is a part schematic view of the orifice covered pipette structure shown in FIGS. 5 and 6 containing a quantity of nutrient broth and disposed within an incubator for additional colony growth.

Referring now to FIGS. 5-7 a slight modification and an additional utilization of the present invention will now be described. In this embodiment, as illustrated in FIG. 5, a Petri dish 50 having a quantity of nutrient agar 51 supporting culture growth in colonies 52 thereon is shown. Pipette 10 is of the same construction as that previously described for the embodiment shown in FIGS. 1-4, and like reference numerals are employed for the same parts thereof. A modified protective plastic cover 57, employed in this embodiment, is provided with an extension tab 58 to permit easy grasping by hand.

In operation of this embodiment, protective plastic cover 57 may be remotely removed by action of plunger 13, as in the previously described embodiment, or cover 57 may be removed by the operator grasping tab 58 thereon and manually removing it. In either removal operation, elastomeric strap 30 maintains cover 57 attached to pipette tube 20. After removal of cover 57 from orifice 27, wire probe 35 is extended via action of plunger 13 and a portion of tip 36 touched or embedded within surface colony 52 in an open petri dish 50.

As illustrated in FIG. 6. The probe wire 35 is then retracted, and orifice 26 of pipette tube 20 is placed into nutrient broth 60 within container 61 and a quantity of sterile broth media 60 is drawn into pipette tube 20 by the pulling action of the plunger 13 acting within syringe barrel 11. Protective cover 57 is then grasped by the operator, utilizing extension tab 58, and again (manually) placed over pipette orifice 25 to hermetically seal the end of pipette tube 20. Plastic cover 57 is designed to stretch fit over pipette tube 20 for hermetically sealing thereof.

Protective cover 57 may be provided with internally and circumferentially disposed ribbed surfaces to act as O-ring seals to assist in maintaining the hermetically sealed condition between the cover and pipette tube end, if so desired. As in the previously described embodiment, the bottom surface of cover 57 is constructed such that puncture thereof by the blunt end 36 of wire probe 35 is prevented during removal of the protective cover 57 by wire probe 35.

After sealing the quantity of nutrient broth 60 within pipette tube 20, the entire pipette 10 is placed within a suitable incubator 70 (FIG. 7) for 18 to 24 hours at 37° C. After incubation, the accumulated growth is uniformly distributed by a back-and-forth rocking motion of pipette 10. After again removing protective cover 27, the growth can be accurately transferred to a number of tubes by a the downward action of syringe plunger 13.

Although the invention has been described as primarily used for the sampling of microbial cultures, the invention is not so limited. Pipette 10 may also be employed to obtain fluid samples in a water column to collect samples at various levels therein, in water pollution studies, industrial sources, such as food processing operations, and the like.

Most of the component parts of the present invention are formed of conventional clear or translucent plastic such as polyvinyl chloride, polyethylene or other rigid plastic. Elastomeric strap 30 in the preferred embodiment is formed of a conventional rubber band, of suitable size and resiliency, to be stressed while covers 27 and 57 are covering orifice 36 and to retract the covers to the side of pipette tube 20 when removed from their covering position. Any conventional bonding or adhesive material, such as commercially available "super glue", may be employed to attach the ends of elastomeric strap 30 to pipette tube 20 and to protective covers 27 and 57 prior to packaging and sterilizing of pipette 10. Pipette 10 may be any of various conventional sizes and the entire pipette is a disposable unit intended to be delivered to the site of use in a sterile condition and adapted for "only-one-use".

The specific embodiments of the invention described herein are intended to be illustrative only and are therefore not to be deemed as exhaustive. There are numerous various modifications and variations of the invention that will be readily apparent to those skilled in the art in the light of the above teachings.

For example, in the embodiment illustrated in FIGS. 5-7, carbohydrate fermentation patterns and antibiotic sensitivity could be determined by arraying along wire probe 35 commercially available disks containing the appropriate dehydrated sugar or antibiotic.

Other changes and modifications of the specific embodiments disclosed herein will be apparent to those skilled in the art. It therefore to be understood that, within the scope of the appended claims, the invention may be practiced other than as specifically described herein.

I claim:

1. A microbial retrieval and sampling device including:
    an elongated pipette having a first and a second end;
    a syringe including a barrel containing a slidable plunger provided at said first end of said pipette;
    a pipette orifice formed at the second end of said pipette;
    an elongated wire probe having a first end secured to said slidable plunger and a second free end disposed adjacent said pipette orifice;
    said elongated wire probe being movable with said slidable plunger between a first portion wherein said free end thereof is disposed within said pipette and a second position wherein said free end of said wire probe extends exteriorly of said pipette orifice;
    external cover means for sealing said pipette orifice;
    said external cover means being slidably removable to expose said pipette orifice under the influence of said wire probe when said wire is extended from said pipette orifice, and
    means elastically retaining said cover means connected to said pipette when said external cover means is removed from said pipette orifice.

2. The microbial retrieval and sampling device of claim 1 wherein said means elastically retaining said cover means connected to said pipette when said cover means is removed from said pipette orifice, comprises an elastomeric member secured to said external cover means and to said pipette; and, said elastomeric member being under tension when said external cover means is disposed over said pipette orifice.

3. A microbial retrieval and sampling device including:
    an elongated pipette having a first and a second end;
    a syringe structure having a barrel containing a slidable plunger disposed at said first end of said elongated pipette;
    an elongated wire probe having a first end secured to said slidable plunger and an unattached second end disposed adjacent said pipette orifice;
    said elongated wire probe being movable with said slidable plunger between a first position wherein said unattached second end is disposed within said pipette and a second position wherein said unattached second end extends exteriorly of said pipette orifice;
    removable cover means connected to said pipette and disposed over said pipette orifice for sealing said orifice; and
    means elastically positioning said removable cover means spaced from said pipette orifice and maintaining said removable cover means connected to said pipette when said cover means is removed from said pipette orifice.

4. The microbial retrieval and sampling device of claim 3 wherein said means elastically positioning said removable cover means spaced from said pipette orifice and maintaining said removable cover means connected to said pipette when said cover means is removed from said pipette orifice comprises an elastomeric member attached to said pipette and to said removable cover means.

5. A microbial retrieval and sampling device including:
    an elongated pipette having a first and a second end;
    a syringe structure having a barrel containing a slidable plunger disposed at said first end of said elongated pipette;
    an elongated wire probe having a first end secured to said slidable plunger and an unattached second end disposed adjacent said pipette orifice;
    said elongated wire probe being movable with said slidable plunger between a first position wherein said unattached second end is disposed within said pipette and a second position wherein said unattached second end extends exteriorly of said pipette orifice;
    removable cover means connected to said pipette and disposed over said pipette orifice;
    means elastically positioning said removable cover means spaced from said pipette orifice and maintaining said removable cover means connected to said pipette when said cover means is removed from said pipette orifice;
    said means elastically positioning said removable cover means spaced from said pipette orifice and maintaining said removable cover means connected to said pipette when said cover means is removed from said pipette orifice comprising an elastomeric member attached to said pipette and to said removable cover means;

said elastomeric member attached to said pipette and to said removable cover means being under tension when said removable cover means is disposed over said pipette orifice; and said elastomeric member being attached to only one edge surface of said removable cover means and serving to elastically position said removable cover means away from said pipette orifice when removed therefrom.

6. The microbial retrieval and sampling device of claim 5 wherein force exerted on said plunger during movement of said wire probe from said first position to said second position causes said elongated wire probe to contact and force said removable cover means away from said pipette orifice.

* * * * *